United States Patent
Carrera Fabra et al.

(10) Patent No.: US 9,333,471 B2
(45) Date of Patent: May 10, 2016

(54) FLUIDICALLY INTEGRATED MAGNETIC BEAD BEATER

(71) Applicant: STAT-DIAGNOSTICA & INNOVATION, S.L., Barcelona (ES)

(72) Inventors: Jordi Carrera Fabra, Barcelona (ES); Anna Comengés Casas, Barcelona (ES); Rafael Bru Gibert, Barcelona (ES); Marta López Fontanals, Barcelona (ES); Gemma Pueyo Castells, Sant Cugat del Vallès (ES); Rupert Maxwell Gaut, Barcelona (ES)

(73) Assignee: STAT—Diagnostica & Innovation, S.L., Barcelona (ES)

( * ) Notice: Subject to any disclaimer, the term of this patent is extended or adjusted under 35 U.S.C. 154(b) by 344 days.

(21) Appl. No.: 13/836,488

(22) Filed: Mar. 15, 2013

(65) Prior Publication Data
US 2013/0272087 A1    Oct. 17, 2013

Related U.S. Application Data

(60) Provisional application No. 61/622,847, filed on Apr. 11, 2012.

(51) Int. Cl.
*B02C 17/24* (2006.01)
*B01F 13/08* (2006.01)
(Continued)

(52) U.S. Cl.
CPC ............ *B01F 13/08* (2013.01); *B01F 11/0082* (2013.01); *B01F 13/0052* (2013.01);
(Continued)

(58) Field of Classification Search
CPC ...... B01F 13/08; B01F 13/0818; B02C 17/24
USPC ............................................ 241/170–184, 2
See application file for complete search history.

(56) References Cited

U.S. PATENT DOCUMENTS 3,356,346 A    12/1967    Landsberger
3,722,831 A     3/1973    Bialas et al.
(Continued)

FOREIGN PATENT DOCUMENTS

CH         663 941 A5      1/1988
DE      101 28 460 A1      1/2003
(Continued)

OTHER PUBLICATIONS

International Search Report for International Application No. PCT/EP2013/057639, European Patent Office, Netherlands, mailed on Aug. 1, 2013.
(Continued)

*Primary Examiner* — Mark Rosenbaum
(74) *Attorney, Agent, or Firm* — Sterne, Kessler, Goldstein & Fox P.L.L.C.

(57) ABSTRACT

A system for at least one of homogenization and lysis of a sample includes one or more walls forming an enclosed chamber, a permanent magnet within the enclosed chamber, a magnet guide, and one or more magnets located outside the chamber. The enclosed chamber has an inlet and one or more fluidic connections configured to introduce at least the sample into the chamber. The permanent magnet has a positive pole and a negative pole. The magnet guide is configured to laterally guide the permanent magnet between a first position and a second position and maintain a substantially constant orientation of the permanent magnet during the movement. Movement of the magnets outside the chamber changes a magnetic field between the one or more magnets and the permanent magnet. The permanent magnet moves between the first and second positions in response to the changing magnetic field.

35 Claims, 17 Drawing Sheets

(51) Int. Cl.
*B01F 11/00* (2006.01)
*B01F 13/00* (2006.01)
*B01F 15/00* (2006.01)
*C12N 1/06* (2006.01)
*C12M 1/00* (2006.01)

(52) U.S. Cl.
CPC ....... *B01F13/0818* (2013.01); *B01F 15/00376* (2013.01); *B01F 15/00876* (2013.01); *B02C 17/24* (2013.01); *C12M 47/06* (2013.01); *C12M 47/08* (2013.01); *C12N 1/066* (2013.01); *B01F 2215/0481* (2013.01)

(56) References Cited

U.S. PATENT DOCUMENTS

| | | | |
|---|---|---|---|
| 3,848,363 A | 11/1974 | Lovness et al. | |
| 3,869,251 A | 3/1975 | Tsantker et al. | |
| 3,907,258 A | 9/1975 | Spaziani | |
| 3,987,967 A | 10/1976 | Kuznetsov et al. | |
| 4,134,553 A | 1/1979 | Steinort et al. | |
| 4,601,431 A | 7/1986 | Watanabe et al. | |
| 4,632,315 A | 12/1986 | Watanabe et al. | |
| 4,632,316 A | 12/1986 | Watanabe et al. | |
| 5,226,744 A | 7/1993 | Kemmerer | |
| 5,383,615 A | 1/1995 | Calka et al. | |
| 6,632,662 B1 | 10/2003 | Broyer et al. | |
| 2011/0070589 A1 | 3/2011 | Belgrader et al. | |

FOREIGN PATENT DOCUMENTS

| | | |
|---|---|---|
| DE | 10 2008 008256 A1 | 4/2009 |
| EP | 0 105 834 A2 | 4/1984 |
| WO | WO 98/39099 A1 | 9/1998 |
| WO | WO 2009/108501 A2 | 9/2009 |
| WO | WO 2011/034621 | 3/2011 |

OTHER PUBLICATIONS

W. Nicholson and P. Setlow, *Molecular Biological Methods for Bacillus*, New York, John Wiley, pp. 391-450, 1990.

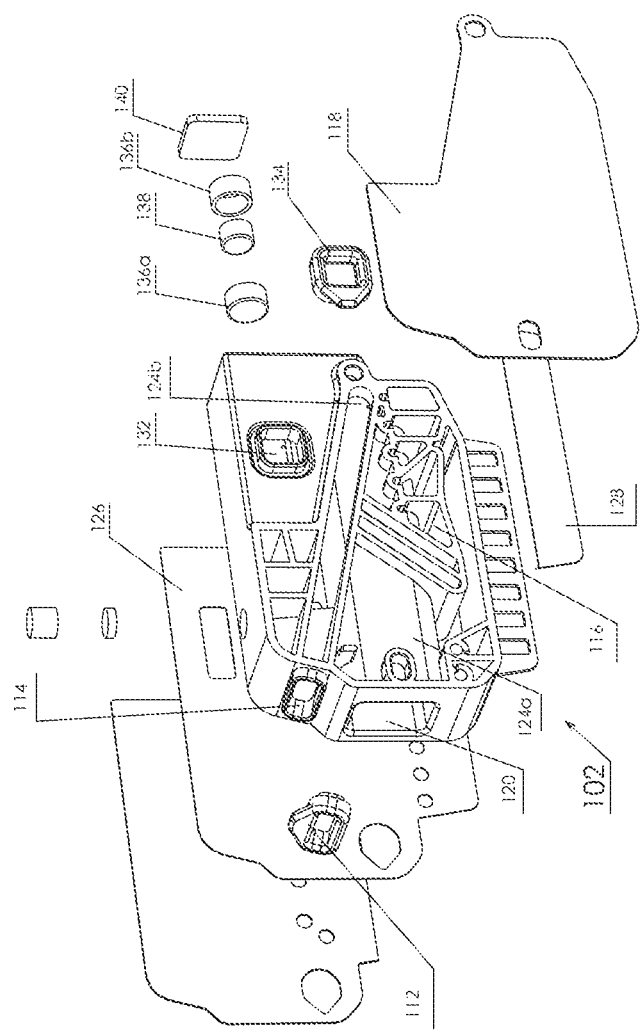

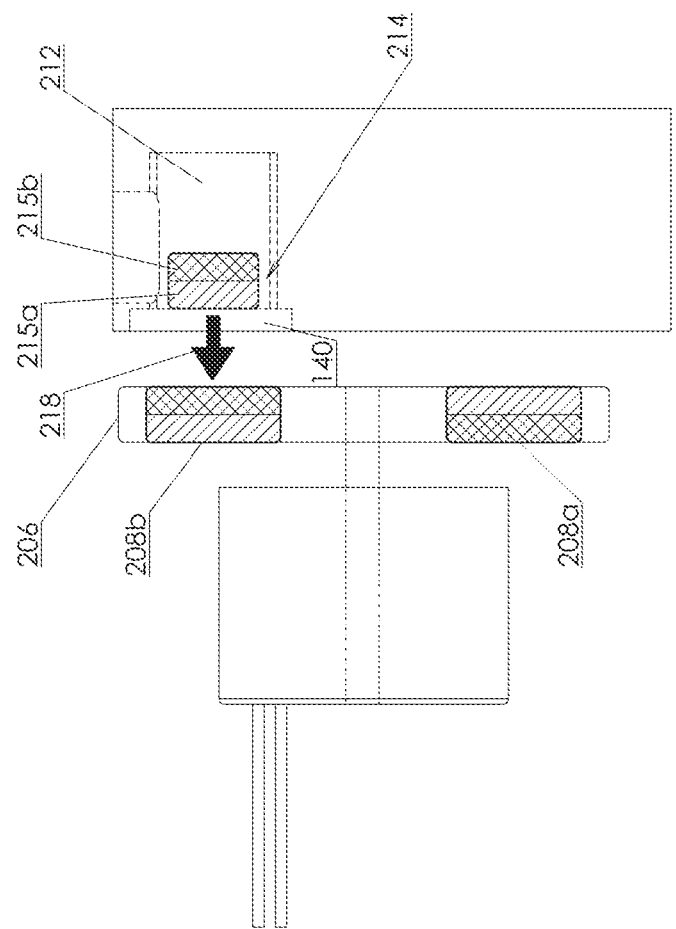

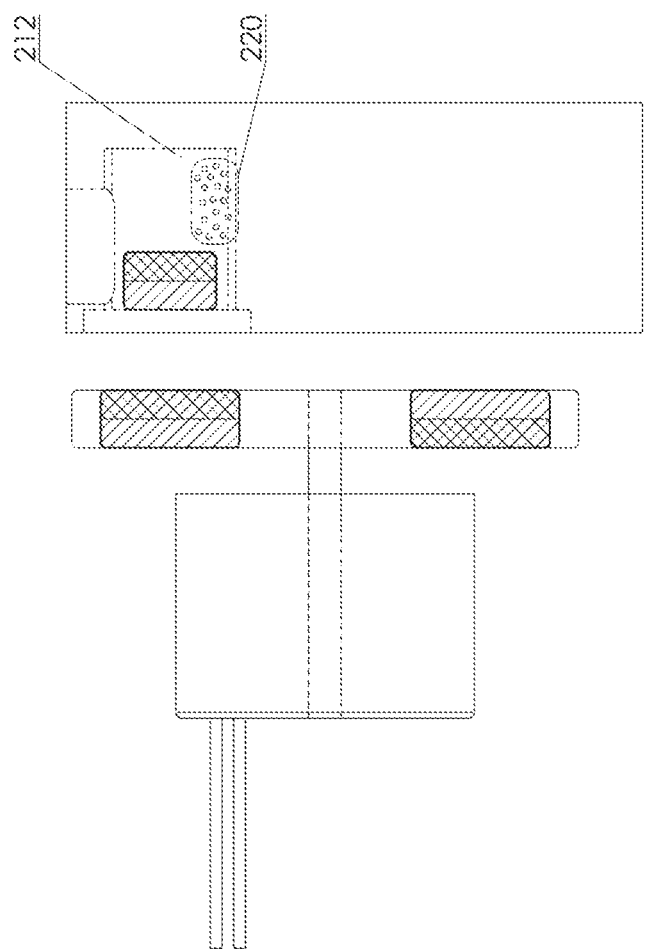

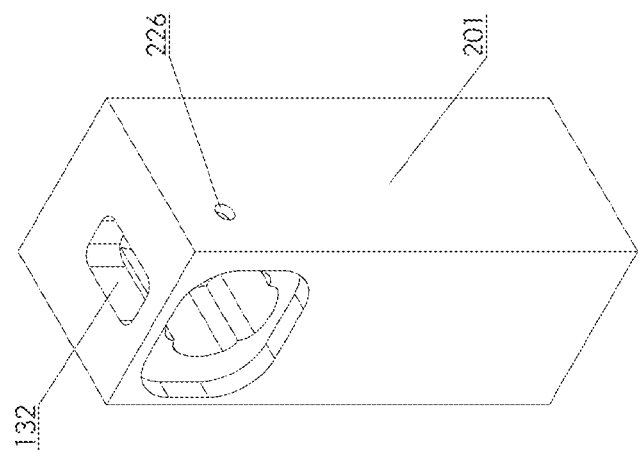

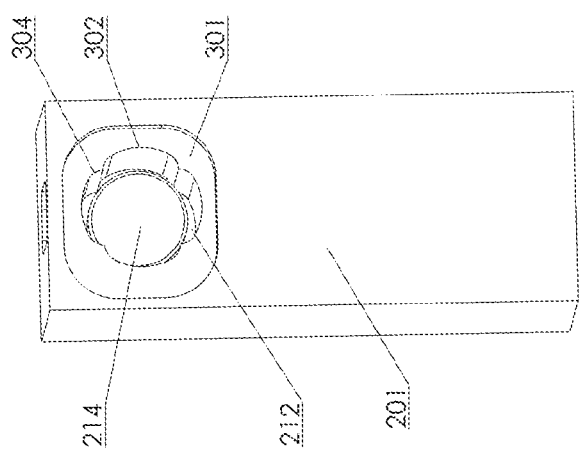

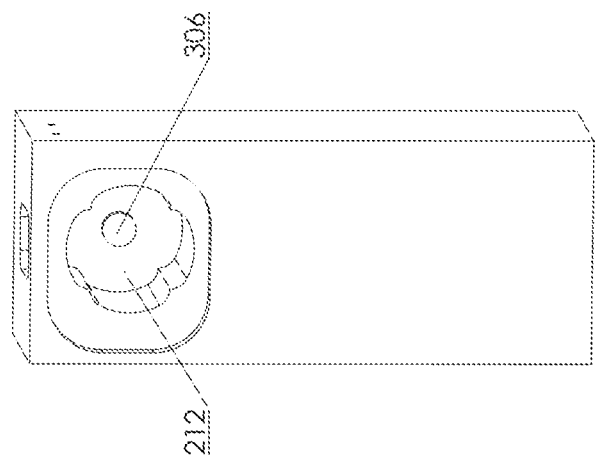

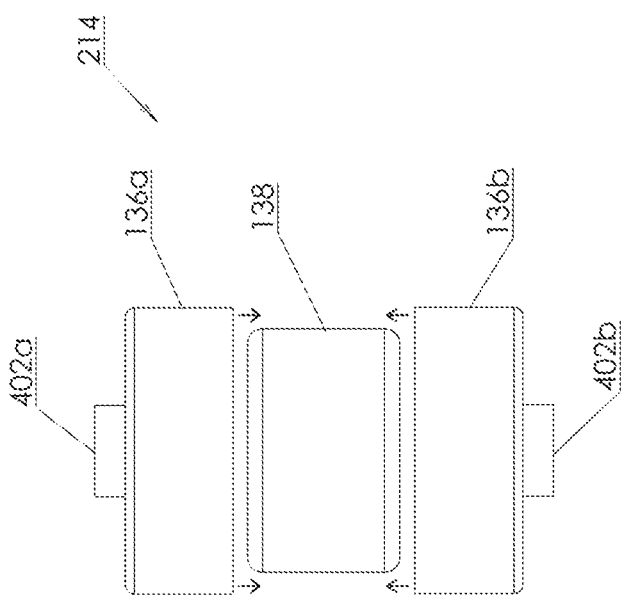

FLUIDICALLY INTEGRATED MAGNETIC BEAD BEATER

CROSS-REFERENCE TO RELATED APPLICATIONS

This application claims the benefit under 35 U.S.C. §119 (e), to provisional application No. 61/622,847 filed on Apr. 11, 2012, the disclosure of which is incorporated by reference herein in its entirety.

BACKGROUND

1. Field

Embodiments of the present invention relate to bead beaters.

2. Background

Given the complexity of the automation of molecular testing and immunoassay techniques, there is a lack of products that provide adequate performance to be clinically usable in near patient testing settings. Typical molecular testing includes various processes involving the correct dosage of reagents, sample introduction, sample homogenization, lysis of cells to extract DNA and/or RNA, purification steps, and amplification for its subsequent detection. Even though there are central laboratory robotic platforms that automate these processes, for many tests requiring a short turnaround time, the central laboratory cannot provide the results in the needed time requirements.

The homogenization and/or lysis of a biological specimen is usually the initial step in a testing process such that a suitably purified analyte or analytes can be obtained for molecular testing. Generally speaking there are three main approaches to cell lysis: chemical, enzymatic and physical. These processes may be used alone or in combination, sequentially or in a single step, to achieve a more optimal process. The use of chemical and enzymatic processes can prove problematic as some chemicals used to rupture the cell wall can denature any enzymes present or generate problems in subsequent processes.

Physical methods for cell rupture include sonication, heating (usually between 90° C.-100° C.), repeated freeze-thawing, creation of rapid and large changes in pressure and mechanical methods. Mechanical methods involve the physical rupture of the cell wall through physical forces such as high-shear forces, grinding, and bombardment of the cell with small particles, often consisting of beads. Mechanical methods of disruption have a number of advantages. They often employ a one-step process, are generally very rapid, are amenable to automation, and have the ability to disrupt solid specimens, such as bone, where the analyte(s) of interests may not be made obtainable without mechanical homogenization.

BRIEF SUMMARY

Mechanical bead beater systems and methods that can be integrated with a near patient testing system are provided.

In an embodiment, a system for at least one of homogenization and lysis of a sample includes one or more walls forming an enclosed chamber, a permanent magnet within the enclosed chamber, a magnet guide, and one or more magnets located outside the chamber. The enclosed chamber has an inlet and one or more fluidic connections configured to introduce at least the sample into the chamber. The permanent magnet has a positive pole and a negative pole. The magnet guide is configured to laterally guide the permanent magnet between a first position and a second position. The magnet guide is also configured to maintain a substantially constant orientation of the positive pole and the negative pole of the permanent magnet during the movement. Movement of the one or more magnets outside the chamber changes a magnetic field between the one or more magnets and the permanent magnet. The permanent magnet is configured to move between the first and second positions in response to the changing magnetic field.

An example method of homogenizing a sample is described. The method includes introducing a sample into an enclosed chamber and actuating one or more magnets located outside the chamber. The magnetic field generated by the one or more magnets induces a force upon a permanent magnet disposed within the chamber, the permanent magnet having a positive pole and a negative pole. The induced force causes the permanent magnet to move. The method further includes laterally guiding the movement of the permanent magnet between a first position and a second position within the chamber. An orientation of the positive pole and the negative pole of the permanent magnet remains substantially constant during the movement. The method further includes homogenizing the sample within the chamber via the movement of the permanent magnet.

Another example method of homogenizing a sample is described. The method includes introducing a sample into an enclosed chamber and actuating one or more magnets located outside the chamber. The magnetic field generated by the one or more magnets induces a force upon a permanent magnet disposed within the chamber, the permanent magnet having a positive pole and a negative pole. The induced force causes the permanent magnet to move. The method further includes laterally guiding the movement of the permanent magnet between a first position and a second position within the chamber. An orientation of the positive pole and the negative pole of the permanent magnet remains substantially constant during the movement. The movement of the permanent magnet excites a plurality of beads located within the chamber. The method further includes homogenizing the sample within the chamber via the movement of the permanent magnet and the plurality of beads.

An example method of lysing a sample is described. The method includes introducing a sample into an enclosed chamber and actuating one or more magnets located outside the chamber. The magnetic field generated by the one or more magnets induces a force upon a permanent magnet disposed within the chamber, the permanent magnet having a positive pole and a negative pole. The induced force causes the permanent magnet to move. The method further includes laterally guiding the movement of the permanent magnet between a first position and a second position within the chamber. An orientation of the positive pole and the negative pole of the permanent magnet remains substantially constant during the movement. The method further includes lysing the sample within the chamber via the movement of the permanent magnet.

Another example method of lysing a sample is described. The method includes introducing a sample into an enclosed chamber and actuating one or more magnets located outside the chamber. The magnetic field generated by the one or more magnets induces a force upon a permanent magnet disposed within the chamber, the permanent magnet having a positive pole and a negative pole. The induced force causes the permanent magnet to move. The method further includes laterally guiding the movement of the permanent magnet between a first position and a second position within the chamber. An orientation of the positive pole and the negative pole of the permanent magnet remains substantially constant during the movement. The movement of the permanent magnet excites a plurality of beads located within the chamber. The method further includes lysing the sample within the chamber via the movement of the permanent magnet and the plurality of beads.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 1 is a graphical representation of a test cartridge platform, according to an embodiment.

FIGS. 2A-F display various views of a bead beater system, according to an embodiment.

FIGS. 3A-C display various other views of the bead beater system, according to an embodiment.

FIGS. 4A-B display a permanent magnet and magnet covers, according to an embodiment.

Figure 2A:
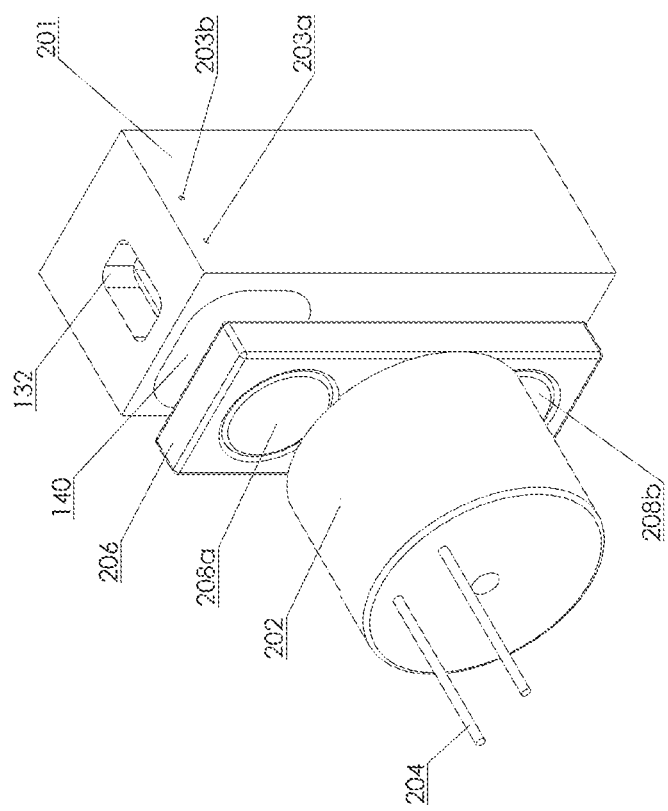

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein relate to a bead beater system for homogenization and/or lysing of a sample. The sample may be a liquid, solid, semi-solid, or a combination thereof. In one embodiment, the bead beater system is integrated with a test cartridge platform. The test cartridge platform includes a network of fluidic channels, a portion of which may couple to the integrated bead beater. The fluidic channels may provide the sample to a bead beater chamber, extract the sample from the bead beater chamber, and/or be used to pressurize or depressurize the bead beater chamber.

The bead-beater system is designed to use physical disruption of samples by the oscillation of, for example, a permanent magnet within the bead-beater chamber. This physical disruption may in turn be aided by the presence of beads (e.g., inert beads made of glass and/or other materials). In one example, the lysis and/or homogenization process is further optimized through the use of a lysis buffer within the bead beater chamber. In another example, enzymatic lysis is performed by applying heat to the sample. Heating the sample may be performed before the actual bead beating of the sample in some examples. In an embodiment, all the necessary reagents and components of the bead-beater are contained within the test cartridge platform.

In some embodiments, both the test cartridge platform and the integrated bead beater are designed to be disposable after use. Once the reagents or the sample are placed within the integrated test cartridge, they do not again enter into contact with the external environment or with any part of an external measurement instrument. This feature is important for many laboratories and hospitals to safely dispose of the products after their use.

The bead-beater chamber itself is designed to be able to process a wide variety of specimens and to disrupt a wide variety of cell types. This is, in part, achieved by the availability of different test cartridge platforms that are specific to each particular specimen/cell type combination. In another example, variable conditions that are controlled by the analyzer, such as the speed and duration of oscillation of the permanent magnet, allow for processing a wide variety of sample types.

Further details relating to the components of the bead beater system are described herein with references made to the figures. It should be understood that the illustrations of each physical component are not meant to be limiting and that a person having skill in the relevant art(s) given the description herein would recognize ways to re-arrange or otherwise alter any of the components without deviating from the scope or spirit of the invention.

FIG. 1 illustrates an example test cartridge system into which a bead beater may be integrated, according to an embodiment. Although reference will be made herein to the structure of the example test cartridge system, one of skill in the art will recognize that bead beater embodiments described herein may be used with any number of testing system types and configurations.

The test cartridge system includes a cartridge housing 102. Other components may be considered as well for inclusion it the test cartridge system, such as an analyzer module or various active components such as pumps or heaters.

Cartridge housing 102 includes a variety of fluidic channels, chambers, and reservoirs. For example, cartridge housing 102 may include a plurality of storage chambers 116 which may contain various buffers or other reagents to be used during an assay or PCR protocol. Storage chambers 116 may be pre-filled with various liquids so that the end user will not need to fill storage chambers 116 before placing the test cartridge system into an analyzer. Cartridge housing 102 may further include one or more processing chambers 124*a-b* connected to fluidic channels along a side of cartridge housing 102. Processing chambers 124*a-b* may be used for a variety of processing and/or waste applications.

Samples are introduced into cartridge housing 102 via sample port 114, according to an embodiment. A user may place a swab completely within sample port 114 and its corresponding chamber 124*b*, and subsequently seal the port with a port lid 112. In another example, sample port 114 receives solid, semi-solid, or liquid samples. In an embodiment, cartridge housing 102 includes more than one inlet to introduce samples.

The various chambers and channels around cartridge housing 102 may be sealed via the use of covers 118, 126, and 128. The covers may be films capable of sealing the fluid within cartridge housing 102. In another example, the covers may be plastic panels. In an example, one or more of the covers are transparent. Additionally, one or more of the covers may be thermally controlled for heating portions of housing 102.

The integrated test cartridge system allows a user to place a sample into, for example, sample port 114, then place the test cartridge system into an analyzer. In embodiments, the reaction steps to be performed including, for example, purification, lysing, mixing, binding, labeling and/or detecting can all be performed within the test cartridge system via interaction with the analyzer without any need for the end user to intervene. Additionally, since all of the liquids remain sealed within the test cartridge system, after the test is completed, the test cartridge system may be removed from the analyzer and safely disposed of without contamination of the analyzer.

The test cartridge system may further include fluidic channels which lead to an inner processing chamber having an opening 132. In an embodiment, the inner processing chamber is an integrated bead beater chamber disposed within cartridge housing 102. Although the chamber itself is hidden from view in FIG. 1, various other components of the system are shown in the exploded view. For example, the bead beater system includes a processing lid 134 that fits over opening 132. Within the chamber itself, a permanent magnet 138 is disposed along with magnet covers 136a-b, according to an embodiment. In another example, a single magnet cover may be used to surround permanent magnet 138. The end of the bead beater chamber is closed using, for example, a panel cover 140. Each of the components of the bead beater system will be explained in more detail herein.

FIGS. 2A-F illustrate various views of the bead beater system, according to embodiments. The description of each view is set forth to describe features that may be present on or within the bead beater system, but should not be limiting as to the placement or dimensional properties of the features.

FIG. 2A provides a perspective view of a bead beater 201 which can be integrated into a test cartridge system, such as example system 100, according to an embodiment. The outer view of bead beater 201 displays panel cover 140 and processing inlet 132 as described previously. In one example, processing inlet 132 may be placed on a side of bead beater 201. Processing inlet 132 is configured to accept any type of sample, including liquid, solid, semi-solid, or any combination thereof. Processing inlet 132 leads into an enclosed chamber where the bead beating process takes place. In another example, samples entering processing inlet 132 are lead to a first chamber, and then transferred from the first chamber into a second chamber where the bead beating process takes place.

On one side of bead beater 201, fluid inlets 203a-b are provided to couple with a fluidic system. For example, fluid inlets 203a-b may couple to channels connecting to any one of storage chambers 116 or processing chambers 124a-b. In an embodiment, fluid inlets 203a-b lead into the chamber where the bead beading takes place. As such, fluid inlets 203a-b may be used for introducing any liquid into the bead beating chamber, extracting any liquid from the bead beating chamber, applying a pressure differential in the bead beating chamber, or any combination thereof.

External to bead beater 201, an actuator system 202 is attached to a beam 206, according to an embodiment. In one example, actuator system 202 is a rotary actuator that applies a rotational force upon beam 206. Actuator system 202 may receive various signals via coupling 204. For example, the signals may include power or control signals. Coupling 204 may represent wires, RF signals, or optical signals. Actuator system 202 may rotate beam 206 at any speed within the capabilities of actuator system 202. In one example, actuator system 202 rotates beam 206 at speeds ranging from 50 RPM to 8000 RPM. In another example, actuator system 202 rotates beam 206 at around 4000 RPM.

Near either end of beam 206, external magnets 208a-b are attached, according to an embodiment. External magnets 208a-b may have the same polarity or opposite polarities. As beam 206 rotates, external magnets 208a-b pass by an outside wall of bead beater 201 in an alternating manner. Thus, a changing magnetic field is generated between the rotating external magnets 208a-b and, for example, a permanent magnet (not shown) disposed within the chamber of bead beater 201.

In one embodiment, bead beater 201 may include a cavity through one of the walls of bead beater 201. The cavity may be covered by a thermally conductive film, such as, for example, an aluminum foil. By heating the thermally conductive film, the contents within the inner processing chamber of bead beater 201 may be heated via the cavity. In another example, one of the walls of the inner processing chamber may be a thermally controlled surface to heat the contents of the inner processing chamber without requiring a cavity. Introducing heat into the inner processing chamber may allow for enzymatic lysis of a sample to occur. In one example, enzymatic lysis may be performed using an applied heat to a sample before the actual bead beating of the sample commences.

Figure 2B:
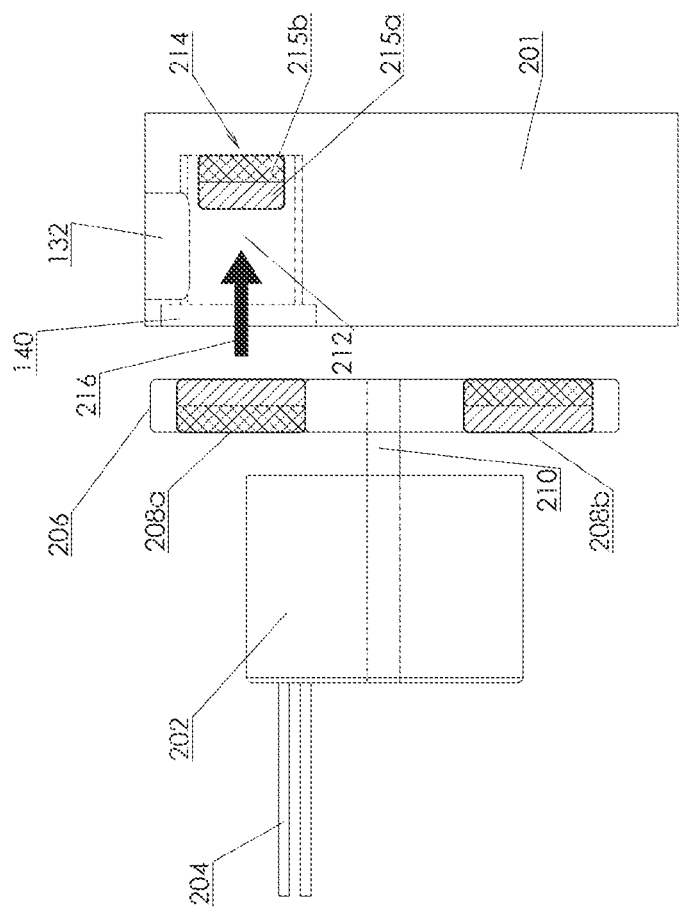

FIG. 2B provides a side cross-sectional view of bead beater 201 along with actuator system 202, according to an embodiment. The view also illustrates a magnetic beater 214 disposed within an enclosed chamber 212 of bead beater 201. Both processing inlet 132 and panel cover 140 are shown as well.

In an embodiment, beam 206 is coupled to actuator system 202 by means of an axle 210 that attaches to the center of beam 206. As previously described, the rotation of beam 206 alternates the passing of external magnets 208a-b outside of enclosed chamber 212. Magnetic beater 214 is a permanent magnet having polarity. In an embodiment, magnetic beater 214 has a positive pole 215a and a negative pole 215b. In an example, each pole of magnetic beater 214 faces either substantially towards or away from panel cover 140.

As beam 206 rotates, the magnetic force induced upon magnetic beater 214 either attracts or repels magnetic beater 214. The attraction or repulsion of magnetic beater 214 causes magnetic beater 214 to move back and forth within enclosed chamber 212. For example, external magnet 208a has a positive polarity and causes magnetic beater 214 to move away due to a magnetic repulsive force 216 between external magnet 208a and positive pole 215a of magnetic beater 214. Magnetic beater 214 may be pushed against the back wall of enclosed chamber 212. In another example, permanent magnet may be pushed to a stop position within enclosed chamber 212 before reaching the back wall.

In one embodiment, one or more walls of enclosed chamber 212 are manufactured from metals having a high thermal conductivity such as aluminum, copper, etc., and can be thermally controlled. Introducing heat into the inner processing chamber may allow for enzymatic lysis of a sample to occur. In one example, enzymatic lysis may be performed using an applied heat to a sample before the actual bead beating of the sample commences.

FIG. 2C illustrates a situation where beam 206 has rotated to bring external magnet 208b outside of enclosed chamber 212. Magnet 208b may have a negative polarity which induces a magnetic attractive force 218 upon magnetic beater 214 due to the attraction between external magnet 208b and positive pole 215a of magnetic beater 214. Magnetic beater 214 may be pulled up against the inner wall of panel cover 140. In another example, magnetic beater 214 may be pulled to a stop position within enclosed chamber 212 before reaching panel cover 140.

The lateral back and forth movement of magnetic beater 214 is guided by the geometry of enclosed chamber 212, according to an embodiment. The geometry may be designed to prevent the face of positive pole 215a and negative pole 215b from flipping within enclosed chamber 212. The movement frequency of magnetic beater 214 within enclosed chamber 212 is associated with the rotation speed of beam 206. Samples placed within enclosed chamber 212 are lysed and/or homogenized by the movement of magnetic beater 214.

FIG. 2D illustrates enclosed chamber 212 having a plurality of beads 220, according to an embodiment. The beads may be included to aid in the homogenization and/or lysing process of a sample within enclosed chamber 212. The back and forth lateral movement of magnetic beater 214 excites plurality of beads 220 into movement as well. Plurality of beads 220 may range in size from one micron in diameter up to 3000 microns in diameter. Additionally, plurality of beads 220 may be manufactured from various inert materials including plastics, glass, ceramics, and silica.

Figure 2E:
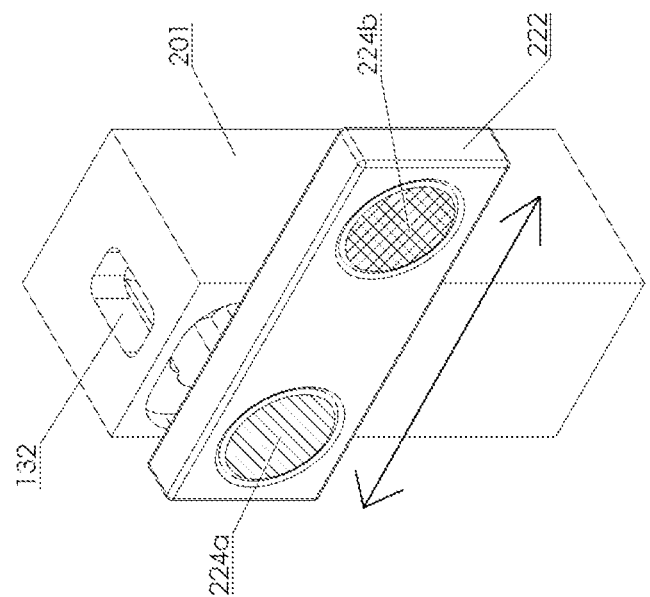

FIG. 2E illustrates another embodiment for actuating a set of external magnets 224a-b. Horizontal beam 222 is connected to a linear actuator (not shown) and lateral back and forth movement of horizontal beam 222 passes external magnets 224a-b by an outside wall of bead beater 201 in an alternating manner, according to an embodiment. Similarly to the discussion above, each of external magnets 224a-b may have opposite polarities, causing magnetic beater 214 to move back and forth within enclosed chamber 212 of bead beater 201. Other alternatives for external magnetic field actuation are also contemplated, such as using an electromagnet to produce an alternating electromagnetic field.

FIG. 2F illustrates another embodiment of bead beater 201 in which a sensor 226 has been included. Sensor 226 may be used to monitor the rate of movement of magnetic beater 214 within enclosed chamber 212. The data collected from sensor 226 is helpful for determining whether magnetic beater 214 is in any way obstructed and/or not moving correctly within enclosed chamber 212. Sensor 226 may be, for example, a magnetic sensor or an optical sensor that identifies movement of magnetic beater 214.

FIG. 3A illustrates a view within enclosed chamber 212 of bead beater 201, according to an embodiment. Magnetic beater 214 is shown surrounded by chamber walls. The geometry of the chamber walls includes lobes 302 and ridges 304 that act as magnet guides, according to an embodiment. Lobes 302 and ridges 304 may be utilized to provide a trefoil or quatrefoil cross-section to the chamber walls. Other arrangements are possible as well for the purpose of guiding the movement of magnetic beater 214. In one example, a recess 301 is provided to accept panel cover 140.

Ridges 304 provide contact points for magnetic beater 214 and prevent magnetic beater 214 from flipping around within enclosed chamber 212. Additionally, ridges 304 reduce wobbling of magnetic beater 214 as it moves laterally within enclosed chamber 212. Ridges 304 may be made of the same material as the rest of chamber walls 302, or may be a softer material, such as Teflon, to reduce mechanical stress on magnetic beater 214.

Lobes 302 provide adequate space around magnetic beater 214 for liquid and beads to move while magnetic beater 214 traverses enclosed chamber 212. The geometry of the chamber walls may include any number of lobes 302. The curvature and general size of lobes 302 may be chosen so as to reduce any dead volume within enclosed chamber 212 during the movement of magnetic beater 214. In one example, the volume existing around magnetic beater 214 within enclosed chamber 212 is 1 ml, though other volumes may be considered as well.

FIG. 3B illustrates the interior of enclosed chamber 212 with magnetic beater 214 removed, according to an embodiment. A protruding element 306 may be included on a back wall of inner chamber 212 to act as a mechanical stop and minimize the contact area of magnetic beater 214 against the back wall. Protruding element 306 protects plurality of beads 220, if included, from being crushed by magnetic beater 214. Protruding element 306 may be any suitable shape and/or size to reduce the contact area as magnetic beater 214 is pushed against the back wall. A second protruding element may also be included on the inner wall of panel cover 140 (not shown).

Figure 3C:
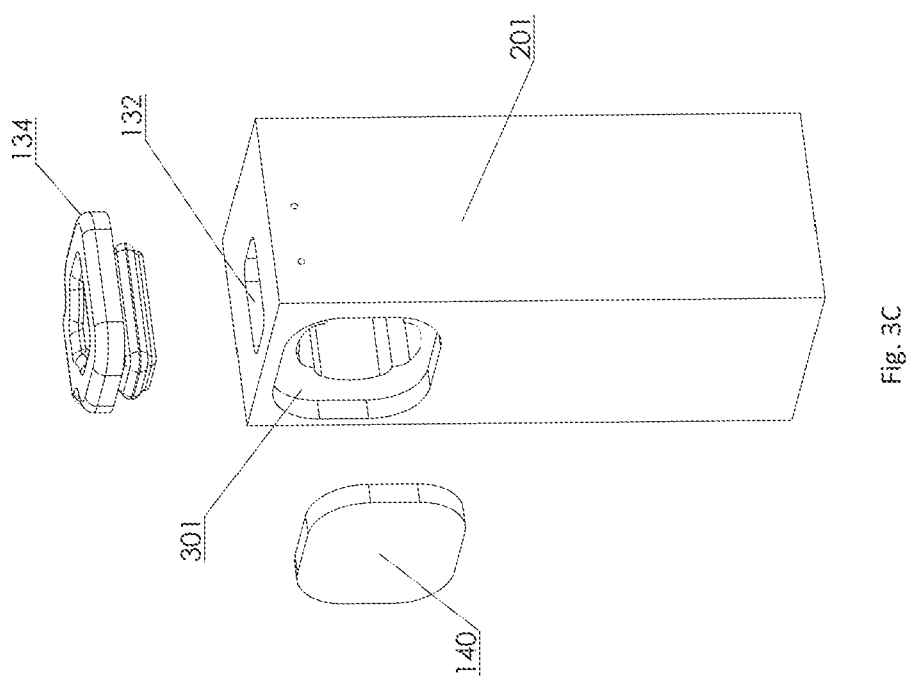

FIG. 3C illustrates a perspective view of bead beater 201 along with processing lid 134 and panel cover 140, according to an embodiment. Processing lid 134 may be dimensioned to seal processing inlet 132 so as to prevent any leakage through processing inlet 132. Panel cover 140 fits into recess 301 to seal the enclosed chamber from the side. In an embodiment, panel cover 140 may be removed in order to remove any objects within the enclosed chamber, such as a permanent magnet.

Figure 4A:
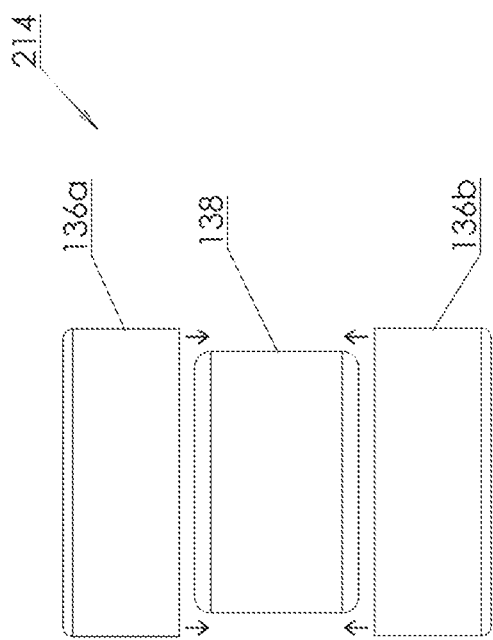

FIG. 4A illustrates a side view of components of magnetic beater 214, according to an embodiment. In an example, magnetic beater 214 includes permanent magnet 138 sandwiched between two magnet covers 136a-b. Permanent magnet 138 may have a substantially cylindrical shape. Magnet covers 136a-b may be utilized to protect permanent magnet 138 from any damage due to collisions within the bead beater system. Magnet covers 136a-b may be made of a compliant material which can absorb the shock caused by magnetic beater 214 colliding with the inner walls or protruding elements 306 of enclosed chamber 212. Magnet covers 136a-b may be coupled together via an adhesive or suitable locking mechanism. In another example, a single magnet cover is used or molded around permanent magnet 138.

FIG. 4B illustrates another embodiment of magnetic beater 214. Magnetic covers 136a-b may include cover protrusions 402a-b. Cover protrusions 402a-b may provide the same mechanical stop benefits as described previously for protruding elements 306.

FIGS. 5-8 describe example methods to be employed for homogenizing or lysing a sample with or without beads, according to embodiments. It should be understood that methods 500, 600, 700, and 800 describe example operation sequences that can be performed with bead beater 201, and should not be considered limiting. Any of methods 800, 900, 1000, and 1100 may also include a step of heating the contents within bead beater 201 to perform an enzymatic lysis. In one example, the enzymatic lysis is performed before the bead beating occurs.

Figure 5:
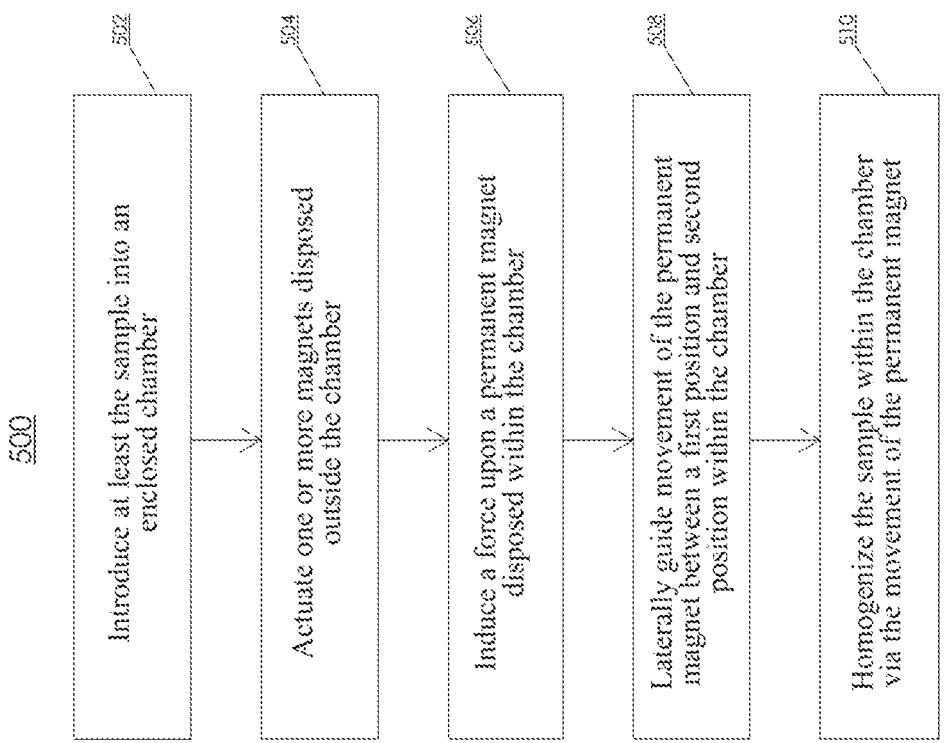
FIGS. 5-8 are diagrams illustrating methods performed by the bead beater system, according to an embodiment.

FIG. 5 displays a flowchart of an example method 500 for homogenizing a sample using bead beater 201.

At block 502, at least the sample is introduced into an enclosed chamber. The sample may be introduced, for example, through processing inlet 132 or via fluid inlets 203a-b. In an embodiment, a solid or semi-solid sample may be provided for homogenization. For example, samples with a high viscosity (e.g. sputum, tissue, bone) are well suited for homogenization to break down complex matrices that hold the cellular components of the sample together.

At block 504, one or more magnets disposed outside the enclosed chamber are actuated. The one or more magnets may be rotated by or linearly translated by an outer wall of the enclosed chamber. Additionally, the one or more magnets may have opposite polarities so as to alternate the direction of an induced magnetic field. Alternatively, an alternating electromagnet may be actuated outside of the enclosed chamber.

At block 506, a force is induced upon a permanent magnet disposed within the chamber. The force is generated due to either magnetic attraction or repulsion.

At block 508, the movement of the permanent magnet is laterally guided between a first position and a second position within the chamber due to the induced magnetic force. The force causes the permanent magnet to move within the chamber in a direction either towards or away from the magnet outside of the chamber walls. The first and second position may correspond to each end of the enclosed chamber. The geometry of the chamber facilitates the lateral movement of the permanent magnet, according to an embodiment.

At block 510, the sample is homogenized within the chamber via the movement of the permanent magnet. The homogenized sample may be lysed using bead beater 201 or transferred to another chamber for further processing.

Figure 6:
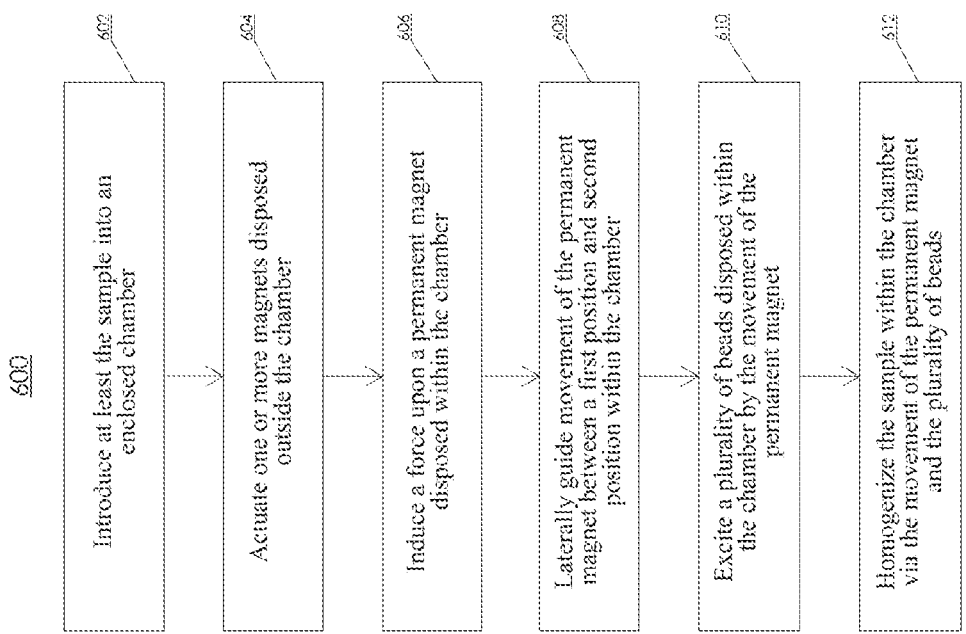

FIG. 6 displays a flowchart of an example method 600 for homogenizing a sample using bead beater 201 containing a plurality of beads. The included beads act to speed up the process of breaking down the sample.

At block 602, at least the sample is introduced into an enclosed chamber. The sample may be introduced, for example, through processing inlet 132 or via fluid inlets 203a-b. In an embodiment, a solid or semi-solid sample may be provided for homogenization. For example, samples with a high viscosity (e.g. sputum, tissue, bone) are well suited for homogenization to break down complex matrices that hold the cellular components of the sample together.

At block 604, one or more magnets disposed outside the enclosed chamber are actuated. The one or more magnets may be rotated by or linearly translated by an outer wall of the enclosed chamber. Additionally, the one or more magnets may have opposite polarities so as to alternate the direction of an induced magnetic field. Alternatively, an alternating electromagnet may be actuated outside of the enclosed chamber.

At block 606, a force is induced upon a permanent magnet disposed within the chamber. The force is generated due to either magnetic attraction or repulsion.

At block 608, the movement of the permanent magnet is laterally guided between a first position and a second position within the chamber due to the induced magnetic force. The force causes the permanent magnet to move within the chamber in a direction either towards or away from the magnet outside of the chamber walls. The first and second position may correspond to each end of the enclosed chamber. The geometry of the chamber facilitates the lateral movement of the permanent magnet, according to an embodiment.

At block 610, a plurality of beads within the chamber are excited by the movement of the permanent magnet. The beads may vary in shape, size and/or material as described previously. The added movement of the beads within the chamber provide further beating of the sample and a more efficient homogenization process.

At block 612, the sample is homogenized within the chamber via the movement of the permanent magnet and the plurality of beads. The homogenized sample may be lysed using bead beater 201 or transferred to another chamber for further processing.

Figure 7:
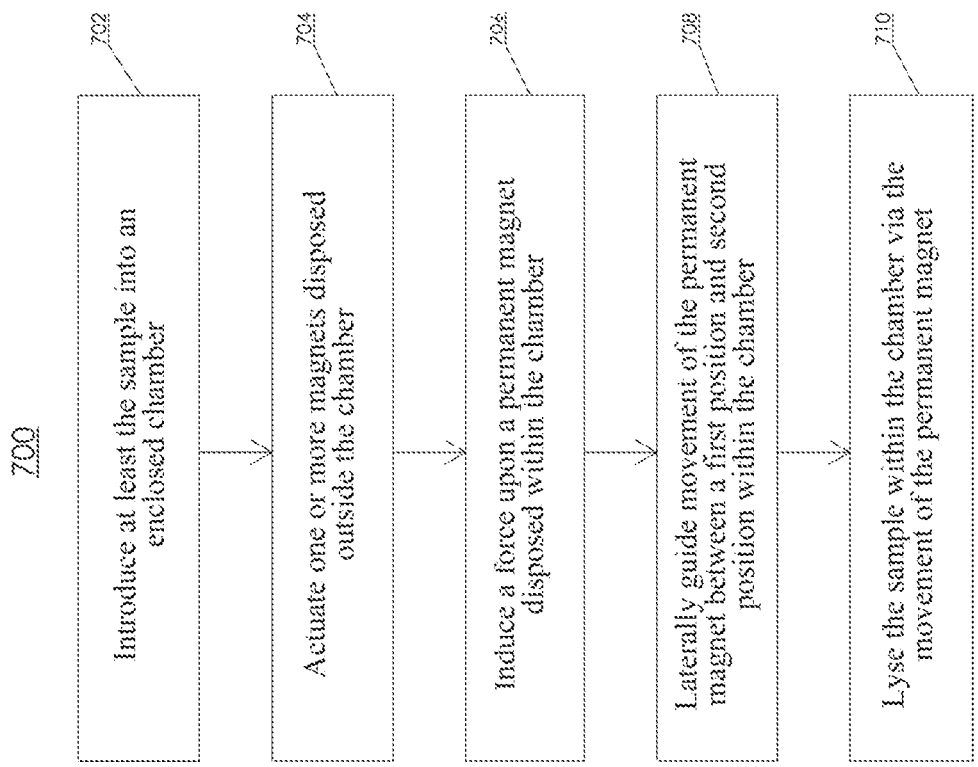

FIG. 7 displays a flowchart of an example method 700 for lysing a sample using bead beater 201. The objective of cell lysis is to release cellular contents which are required for analysis. Examples of cellular contents include, but are not limited to, DNA, RNA, polypeptides, enzymes, prions, proteins, antibodies, antigens, allergens, and virons.

At block 702, at least the sample is introduced into an enclosed chamber. The sample may be introduced, for example, through processing inlet 132 or via fluid inlets 203a-b.

At block 704, one or more magnets disposed outside the enclosed chamber are actuated. The one or more magnets may be rotated by or linearly translated by an outer wall of the enclosed chamber. Additionally, the one or more magnets may have opposite polarities so as to alternate the direction of an induced magnetic field. Alternatively, an alternating electromagnet may be actuated outside of the enclosed chamber.

At block 706, a force is induced upon a permanent magnet disposed within the chamber. The force is generated due to either magnetic attraction or repulsion.

At block 708, the movement of the permanent magnet is laterally guided between a first position and a second position within the chamber due to the induced magnetic force. The force causes the permanent magnet to move within the chamber in a direction either towards or away from the magnet outside of the chamber walls. The first and second position may correspond to each end of the enclosed chamber. The geometry of the chamber facilitates the lateral movement of the permanent magnet, according to an embodiment.

At block 710, the sample is lysed within the chamber via the movement of the permanent magnet. The lysate may be transferred from the chamber to a second chamber via one of fluid inlets 203a-b.

Figure 8:
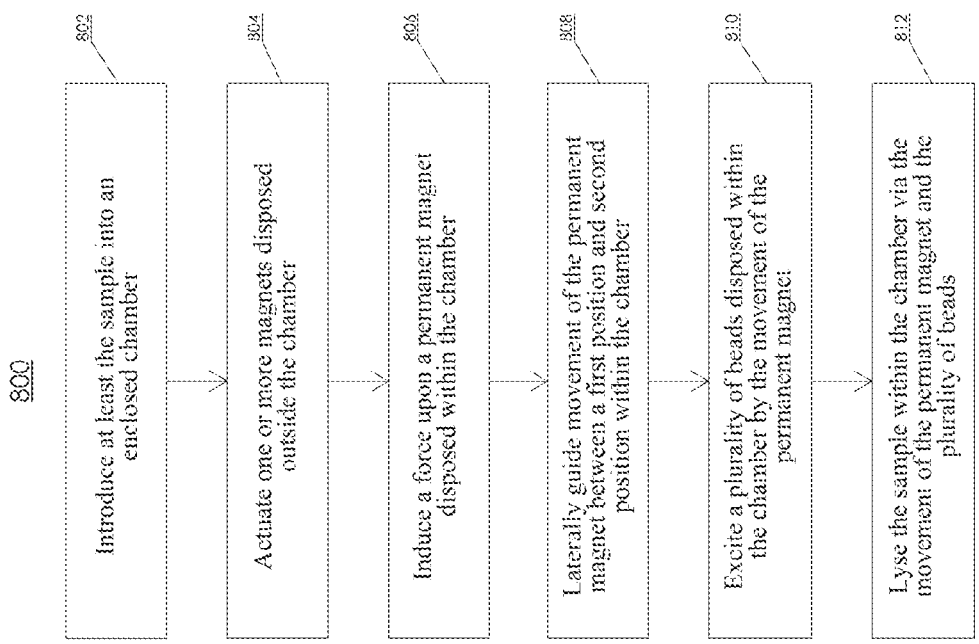

FIG. 8 displays a flowchart of an example method 800 for lysing a sample using bead beater 201 containing a plurality of beads. The objective of cell lysis is to release cellular contents which are required for analysis. Examples of cellular contents include, but are not limited to, DNA, RNA, polypeptides, enzymes, prions, proteins, antibodies, antigens, allergens, and virons. The included beads act to speed up the process of tearing the cell walls to release the cellular contents.

At block 802, at least the sample is introduced into an enclosed chamber. The sample may be introduced, for example, through processing inlet 132 or via fluid inlets 203a-b.

At block 804, one or more magnets disposed outside the enclosed chamber are actuated. The one or more magnets may be rotated by or linearly translated by an outer wall of the enclosed chamber. Additionally, the one or more magnets may have opposite polarities so as to alternate the direction of an induced magnetic field. Alternatively, an alternating electromagnet may be actuated outside of the enclosed chamber.

At block 806, a force is induced upon a permanent magnet disposed within the chamber. The force is generated due to either magnetic attraction or repulsion.

At block 808, the movement of the permanent magnet is laterally guided between a first position and a second position within the chamber due to the induced magnetic force. The force causes the permanent magnet to move within the chamber in a direction either towards or away from the magnet outside of the chamber walls. The first and second position may correspond to each end of the enclosed chamber. The geometry of the chamber facilitates the lateral movement of the permanent magnet, according to an embodiment.

At block 810, a plurality of beads within the chamber are excited by the movement of the permanent magnet. The beads may vary in shape, size and/or material as described previously. The added movement of the beads within the chamber provide further beating of the cells and lead to a more efficient lysing process.

At block 812, the sample is lysed within the chamber via the movement of the permanent magnet and the plurality of beads. The lysate may be transferred from the chamber to a second chamber via one of fluid inlets 203a-b.

EXAMPLE

An Example protocol to be performed using embodiments of bead beater 201 is now discussed. The protocol is an example only and is not limiting on embodiments of the present invention. The lysing efficiency of the bead beater with different bead sizes is analyzed based on DNA detection. It should be understood that the steps recited here provide just one possible example for using the system.

*Bacillus subtilis*, known also as the hay *bacillus* or grass *bacillus*, is a Gram-positive, catalase-positive bacterium. A member of the genus *Bacillus*, *B. subtilis* is rod-shaped, and has the ability to form a tough, protective endospore, allowing the organism to tolerate extreme environmental conditions. Endospores of various *Bacillus* species are formed in sporulation, a process that is generally induced by reduced levels of nutrients in the environment. Endospores contain an outer spore cortex that is extremely resistant to harsh physical and chemical treatments making it challenging to identify a spore lysis method that can be completed in a few minutes.

An example protocol for lysing the cells of *Bacillus subtilis* is adapted from W. Nicholson and P. Setlow, *Molecular Biological Methods for Bacillus*, New York, John Wiley, pp. 391-450, 1990. In this example protocol, a 100 mL culture of *Bacillus subtilis* subsp. *spizizenii* (ATCC 6633) grown in sporulation medium (SM) is vortexed, then separated in two volumes of 50 mL. After centrifugation at 3750 g for 15 minutes, the pellets are washed three to five times with 50 mL sterile cold distilled water, each wash being centrifuged at 3750 g for 15 minutes. The final pellets are re-suspended in 50 mL of sterile cold distilled water. Spore suspensions are treated with DNase to remove external residual DNA, quantified and diluted to a final concentration of $5 \times 10^9$ endospores/mL. Serial 10-fold-dilutions are prepared ($1 \times 10^4$, $1 \times 10^3$, $1 \times 10^2$, and 10 endospores/mL) in nucleases free water to be used as a starting material in the fluidically integrated magnetic bead beater.

First, 400 mg of sterile, acid washed glass beads are introduced into the bead beater chamber. Second, a 400 μL endospores dilution is transferred to the bead beater chamber via the processing inlet. The magnets on the outside of the bead beater are rotated at around 4000 RPM for about 1 minute to perform lysis on the cells within the bead beater chamber. Bacterial nucleic acids are released when spores are disrupted by the mechanical action of the bead beater. Nucleic acid extractions remain stable for several months when stored frozen at −80° C. or −20° C. and may be frozen and thawed several times without any significant loss in PCR analytical sensitivity.

Amplification and detection of DNA from *Bacillus subtilis* endospores at different starting concentrations is performed on the StepOnePlus™ Real-Time PCR System from Applied Biosystems with the TaqMan® Universal master mix II no UNG, with Taq Gold polymerase (from Applied Biosystems, ref 4440040), according to the manufacturer's instructions. 1.5 μL of prepared lysate is added directly to a qPCR reaction having 1× TaqMan® Universal master mix II no UNG with Taq Gold polymerase, 0.90 μM of each SpoA *Bacillus subtilis*-specific primer, 0.25 μM of SpoOA TaqMan® probe, and 0.8 mg/mL BSA; in a final volume of 15 μL. In parallel, spores without processing are tested as untreated controls (at the same concentrations). 1.5 μL of distilled water is also added to a qPCR reaction as a negative control. The optimal cycling conditions for maximum sensitivity and specificity are 10 minutes at 95° C. for initial denaturation, then fifty cycles of two steps consisting of 15 seconds at 95° C. and 60 seconds at 60° C. Amplification is monitored during each elongation cycle by measuring the level of fluorescence. Table 1 below provides the SpoOA *Bacillus subtilis*-specific primers and probe sequence used in the TaqMan® qPCR reaction.

TABLE 1

| Primer | Sequence (5'->3') | Length (bp) | Product size (bp) |
|---|---|---|---|
| SpoOA F | ccatcatcgcaaagcagtatt | 21 | 70 |
| SpoOA R | tgggacgccgatttcatg | 18 | |
| SpoOA probe | ctcgacgcgagcatcacaagcatt | 24 | |

Figure 9:
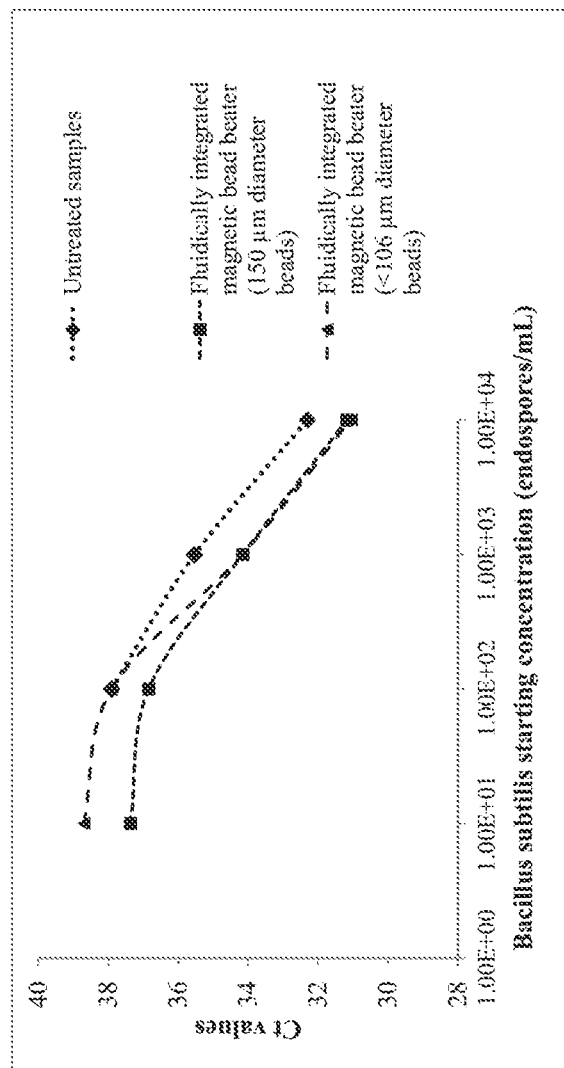
FIG. 9 is a graph of Ct values from *Bacillus subtilis* spores.

FIG. 9 provides a graph of the Ct values (number of PCR cycles needed to produce a positive signal) for samples processed with various sizes beads, and untreated samples, at four different *B. subtilis* starting concentrations. Results are a mean of 10 replicates at each concentration.

At low *Bacillus subtilis* concentrations (10 and $1 \times 10^2$ endospores/mL), Ct values were lower in the presence of 150-212 μm diameter beads (higher DNA concentration) compared to the <106 μm diameter bead conditions, increasing the sensitivity of the process. At higher concentrations ($1 \times 10^3$ and $1 \times 10^4$ endospores/mL) no difference was observed between the two bead sizes tested. The larger bead size (150-212 μm diameter) consistently produced lower Ct values than the untreated samples for each starting concentration of *Bacillus subtilis*, while the smaller bead size (<106 μm diameter) produced lower Ct values than the untreated samples only for the higher starting concentrations ($1 \times 10^3$ and $1 \times 10^4$ endospores/mL.) Untreated samples were undetectable at the lowest *Bacillus subtilis* concentration (10 endospores/mL.)

The best results in terms of sensitivity and lysis efficiency are observed with the fluidically integrated magnetic bead beater having 150-212 μm diameter silica beads, in this example.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

What is claimed is:

1. A system for at least one of homogenization and lysis of a sample comprising:
   one or more walls forming an enclosed chamber having an inlet and one or more fluidic connections configured to introduce at least the sample into the chamber;
   a permanent magnet having a positive pole and a negative pole and disposed within the chamber;
   a magnet guide configured to laterally guide the permanent magnet between a first position and a second position, and to maintain a substantially constant orientation of the positive pole and the negative pole of the permanent magnet during the movement; and
   one or more magnets disposed outside the chamber,
   wherein movement of the one or more magnets changes a magnetic field between the one or more magnets and the permanent magnet, and wherein the permanent magnet is configured to laterally move between the first and second positions in response to the changing magnetic field, and wherein the permanent magnet is configured to excite a plurality of beads disposed within the chamber when the permanent magnet moves laterally between the first and second positions.

2. The system of claim 1, wherein the magnet guide is formed by an interior shape of the one or more walls.

3. The system of claim 2, wherein a cross-section of the interior shape of the one or more walls has a substantially trefoil shape.

4. The system of claim 2, wherein a cross-section of the interior shape of the one or more walls has a substantially quatrefoil shape.

5. The system of claim 1, wherein one or more walls of the chamber comprise one or more protruding elements at both the first position and the second position.

6. The system of claim 5, wherein the one or more protruding elements are configured to contact the permanent magnet as it moves between the first and second positions.

7. The system of claim 1, wherein the inlet is configured to allow for the introduction of solid, semi-solid, or liquid samples into the chamber from the outside environment.

8. The system of claim 7, further comprising a cap dimensioned to fit over the inlet and configured to prevent leakage through the inlet.

9. The system of claim 1, wherein at least a portion of the one or more fluidic connections are configured to pressurize or depressurize the chamber.

10. The system of claim 1, wherein the one or more fluidic connections are further configured to introduce at least the sample from a first reservoir into the chamber.

11. The system of claim 1, further comprising one or more other fluidic connections configured to expel at least the sample from the chamber.

12. The system of claim 11, wherein the one or more other fluidic connections are further configured to expel at least the sample from the chamber to a second reservoir.

13. The system of claim 1, wherein the permanent magnet has a substantially cylindrical shape.

14. The system of claim 1, further comprising a protective cover sealed around the permanent magnet.

15. The system of claim 14, wherein the protective cover comprises one or more protruding elements.

16. The system of claim 15, wherein the one or more protruding elements are configured to contact ends of the chamber as the permanent magnet moves between the first and second positions.

17. The system of claim 1, wherein the plurality of beads comprise materials selected from the group consisting of plastic, glass, ceramic, and silica.

18. The system of claim 1, wherein the plurality of beads range in diameter from 1 micron up to approximately 3000 microns.

19. The system of claim 1, wherein the one or more magnets disposed outside the chamber are coupled to a rotary actuator.

20. The system of claim 19, wherein the rotary actuator rotates the one or more magnets at a speed ranging from 50 to 8000 RPM.

21. The system of claim 1, wherein the one or more magnets disposed outside the chamber are coupled to a linear actuator.

22. The system of claim 1, further comprising a sensor configured to measure a rate of movement of the permanent magnet within the chamber.

23. The system of claim 1, wherein the one or more magnets are electromagnets.

24. The system of claim 1, further comprising a cavity disposed on a side of the enclosed chamber, such that a heated surface placed against the cavity substantially raises the temperature within the enclosed chamber.

25. A system for at least one of homogenization and lysis of a sample comprising:
   one or more walls forming an enclosed chamber having an inlet and one or more fluidic connections configured to introduce at least the sample into the chamber;
   a permanent magnet having a positive pole and a negative pole and disposed within the chamber;
   a magnet guide configured to laterally guide the permanent magnet between a first position and a second position, and to maintain a substantially constant orientation of the positive pole and the negative pole of the permanent magnet during the movement;
   one or more magnets disposed outside the chamber; and
   a sensor configured to measure a rate of movement of the permanent magnet within the chamber,
   wherein movement of the one or more magnets changes a magnetic field between the one or more magnets and the permanent magnet, and wherein the permanent magnet is configured to laterally move between the first and second positions in response to the changing magnetic field.

26. The system of claim 25, wherein the magnet guide is formed by an interior shape of the one or more walls.

27. The system of claim 25, wherein one or more walls of the chamber comprise one or more protruding elements at both the first position and the second position.

28. The system of claim 25, wherein at least a portion of the one or more fluidic connections are configured to pressurize or depressurize the chamber.

29. The system of claim 25, wherein the one or more fluidic connections are further configured to introduce at least the sample from a first reservoir into the chamber.

30. The system of claim 25, further comprising one or more other fluidic connections configured to expel at least the sample from the chamber.

31. The system of claim 30, wherein the one or more other fluidic connections are further configured to expel at least the sample from the chamber to a second reservoir.

32. The system of claim 25, further comprising a protective cover sealed around the permanent magnet.

33. The system of claim 25, wherein the permanent magnet is configured to excite a plurality of beads disposed within the chamber when the permanent magnet moves laterally between the first and second positions.

34. The system of claim 25, wherein the one or more magnets disposed outside the chamber are coupled to a rotary actuator.

35. The system of claim 25, further comprising a cavity disposed on a side of the enclosed chamber, such that a heated surface placed against the cavity substantially raises the temperature within the enclosed chamber.

* * * * *